US012797009B2

(12) United States Patent
Mäkinen

(10) Patent No.: US 12,797,009 B2
(45) Date of Patent: Nov. 17, 2026

(54) OPTICAL SENSING IN A WEARABLE DEVICE

(71) Applicant: Oura Health Oy, Oulu (FI)

(72) Inventor: Jukka Tapani Mäkinen, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 19/207,195

(22) Filed: May 13, 2025

(65) Prior Publication Data

US 2025/0352145 A1 Nov. 20, 2025

Related U.S. Application Data

(60) Provisional application No. 63/649,231, filed on May 17, 2024.

(51) Int. Cl.
*A61B 5/00* (2006.01)

(52) U.S. Cl.
CPC .......... *A61B 5/6826* (2013.01); *A61B 5/0075* (2013.01); *A61B 2562/0238* (2013.01); *A61B 2562/0242* (2013.01); *A61B 2562/043* (2013.01)

(58) Field of Classification Search
CPC ................ A61B 5/6826; A61B 5/0075; A61B 2562/0238; A61B 2562/0242; A61B 2562/043; A61B 5/02416; A61B 5/02427; A61B 5/14552
See application file for complete search history.

(56) References Cited

U.S. PATENT DOCUMENTS

2016/0233447 A1* 8/2016 Kim .................. A61B 5/02427
2016/0313798 A1* 10/2016 Connor ............... A61B 5/0059
2016/0317060 A1* 11/2016 Connor ................. A61B 5/053
2018/0042513 A1* 2/2018 Connor ............... A61B 5/0537
2020/0000345 A1* 1/2020 Connor ............. A61B 5/14532
2020/0329985 A1 10/2020 Wong et al.
2023/0113714 A1 4/2023 Vallius et al.
2024/0090835 A1* 3/2024 Watanabe ........... A61B 5/6826

FOREIGN PATENT DOCUMENTS

GB 2622396 A * 3/2024 .......... G06N 3/0475
WO 2024/071696 A1 4/2024

OTHER PUBLICATIONS

"International Search Report and Written Opinion of the International Searching Authority," issued in connection with Int'l Appl. No. PCT/US2025/029407, dated Sep. 9, 2025 (9 pages).

* cited by examiner

*Primary Examiner* — Christopher Koharski
*Assistant Examiner* — James F McDonald, III
(74) *Attorney, Agent, or Firm* — ArentFox Schiff LLP

(57) ABSTRACT

Methods, systems, and devices for operating a wearable device are described. A wearable device may include an optoelectronic-transmitter configured to output an optical signal with a narrow angular spread. The optoelectronic-transmitter may be at least partially covered with a material protrusion that has at least one dimension based on the angular spread. The wearable device may include an aperture within an inner surface of a housing of the wearable device. The aperture may be configured to enable propagation of the optical signal through the housing, and a width of the aperture may be based on the angular spread such that the aperture permits propagation of the optical signal within the angular spread. An optoelectronic-detector configured to receive the optical signal may be disposed at a distance from the optoelectronic-transmitter that is based on the angular spread.

20 Claims, 5 Drawing Sheets

400-a 400-b

400

OPTICAL SENSING IN A WEARABLE DEVICE

CROSS REFERENCE

The present Application for Patent claims the benefit of U.S. Provisional Patent Application No. 63/649,231 by Makinen, entitled "OPTICAL SENSING IN A WEARABLE DEVICE," filed May 17, 2024, assigned to the assignee hereof and expressly incorporated by reference herein.

FIELD OF TECHNOLOGY

The following relates to wearable devices and data processing, including optical sensing in a wearable device.

BACKGROUND

A wearable device may be configured to collect biometric data from a user by transmitting optical signals into the skin of the user. Improved techniques for collecting biometric data using optical signals may be desired.

DETAILED DESCRIPTION

Figure 1:
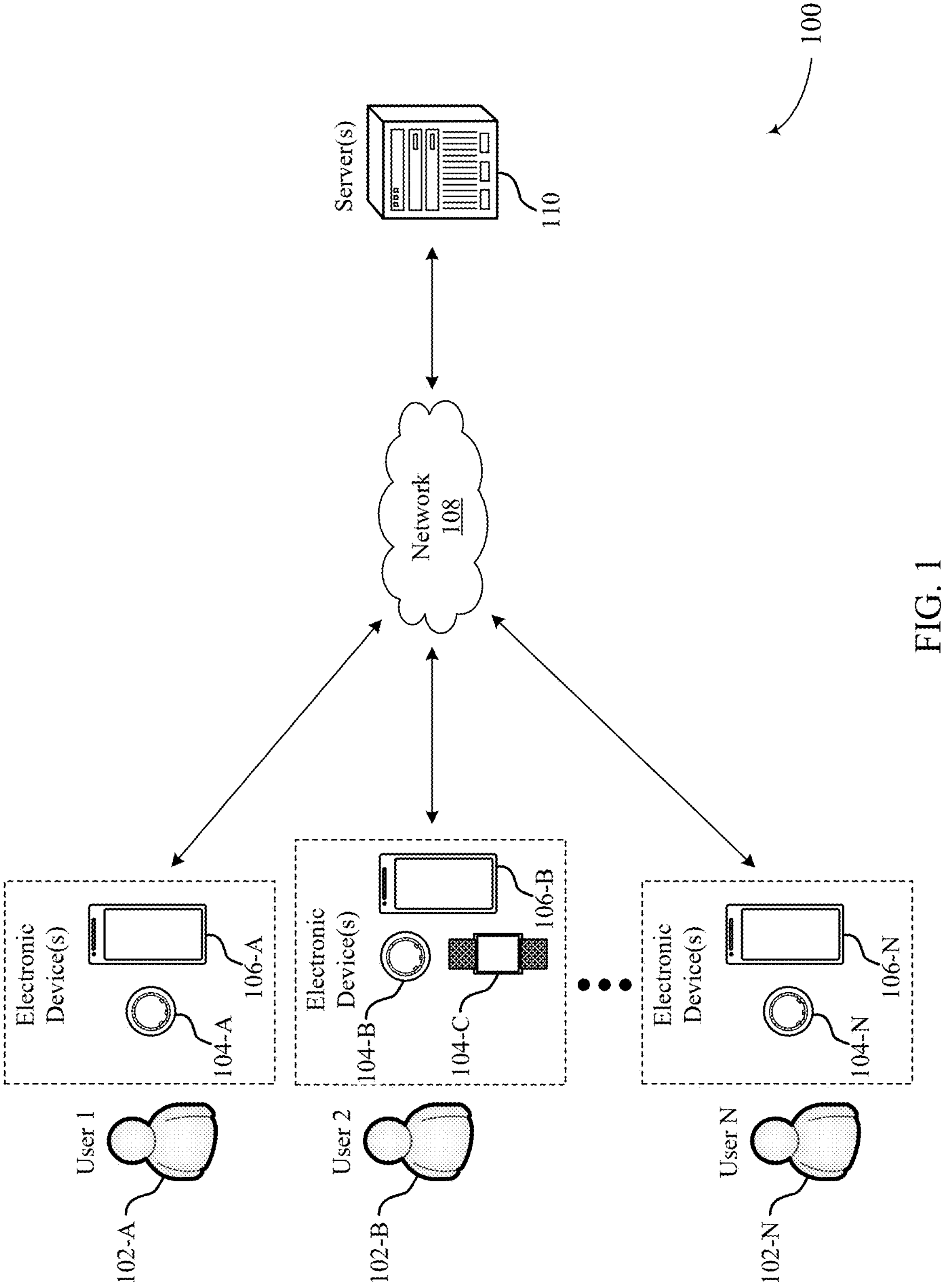
FIG. 1 illustrates an example of a system that supports optical sensing in a wearable device in accordance with aspects of the present disclosure.

A wearable device may collect biometric data from a user by transmitting wide-beam optical signals (e.g., via wide-beam optoelectronic-transmitters) into the skin of the user and measuring various characteristics of the optical signals reflected back into optoelectronic-detectors. To accommodate the wide-beam optical signals (e.g., optical signals having beams with full-width half-measure angular spread greater than 80° in polar coordinates), the apertures for the optoelectronic-transmitters may also be relatively wide. However, relatively wide apertures may increase the proportion of optical signals that is reflected into the optoelectronic sensors through the wearable device, a phenomenon referred to as internal stray light, which may decrease the quality of the biometric data collected by the wearable device. Further, only a fraction of the wide-beam optical signals may reach deep enough into the skin to enable biometric data collection. Although such a phenomenon may be partially compensated for by placing the optoelectronic-transmitters at large distances from the optoelectronic-detectors, such a design may be difficult to manufacture and may not be possible in smaller form factor devices such as wearable ring devices.

According to the designs described herein, a wearable device may use one or more narrow-beam optoelectronic-transmitters to transmit narrow-beam optical signals (e.g., optical signals having beams with full-width half-measure angular spread less than 20° in polar coordinates) for the collection of biometric data. Relative to wide-beam optical signals, use of narrow-beam optical signals may enable small apertures (e.g., apertures proportionally sized relative to the beam width), which may decrease the internal stray light in the wearable device, thereby improving biometric data collection quality. Further, the proportion of narrow-beam optical signals that reach deep enough into the skin to enable biometric data collection may be higher than the proportion of wide-beam optical signals, which may improve the quality of biometric data collection. Increased penetration into the skin may also enable reduced distances between the narrow-beam optoelectronic-transmitters and the optoelectronic-detectors, which may decrease manufacturing complexity and support smaller form factor devices such as wearable ring devices.

In some implementations, wearable devices (e.g., wearable ring devices) may include both narrow-beam optoelectronic-transmitters and wide-beam light sources (such as light-emitting diodes (LEDs)). In such cases, the wearable device may be able to monitor the relative quality of physiological data measured from the user using the narrow-beam and wide-beam light sources, and may selectively activate or deactivate the narrow-beam and wide-beam light sources based on the relative quality of data. That is, the wearable device may be able to switch between narrow-beam and wide-beam light sources for collecting physiological data (e.g., based on relative quality of data collected from the respective types of light sources, based on the power consumption of the respective types of light sources, etc.), which may result in more accurate and reliable physiological data, improved battery life/performance, etc.

Aspects of the disclosure are initially described in the context of systems supporting physiological data collection from users via wearable devices. Additional aspects of the disclosure are described with reference to wearable devices and plots. Aspects of the disclosure are further illustrated by and described with reference to apparatus diagrams, system diagrams, and flowcharts that relate to optical sensing in a wearable device.

FIG. 1 illustrates an example of a system 100 that supports optical sensing in a wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data (also referred to as biometric data), 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols. Moreover, in some cases, the wearable device 104 and the user device 106 may be included within (or make up) the same device. For example, in some cases, the wearable device 104 may be configured to execute an application associated with the wearable device 104, and may be configured to display data via a GUI.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, optoelectronic-transmitters, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

According to the designs described herein, the light-emitting components included in the wearable device 104 may be narrow-beam optoelectronic-transmitters that output narrow-beam optical signals for biometric data collection. Examples of narrow-beam optoelectronic-transmitters include vertical-cavity surface-emitting laser (VCSELs), laser diodes, narrow-beam light-emitting diodes (LEDs), and resonant cavity light emitting diodes (RCLEDs). Use of narrow-beam optoelectronic-transmitters may allow the size of the apertures for the optoelectronic-transmitters to be reduced without signal-clipping (e.g., without the aperture boundaries blocking the outgoing optical signals), which in turn may reduce the amount of internal stray light reflected into the optoelectronic-detectors. Additionally, compared to wide-beam optical signals, narrow-beam optical signals may have greater penetration depth into a tissue of the user. So, use of narrow-beam optoelectronic-transmitters may allow for a higher proportion of narrow-beam optical signals to penetrate into the signal-relevant (e.g., venous pulsating layers) of the user's skin, which in turn may improve the quality of biometric data collection, reduce power consumption, and allow for reduced distances between the optoelectronic-transmitters and the optoelectronic-detectors, among other advantages. Because a larger proportion of the optical signals reach signal-relevant depths, the power consumed by the optoelectrical-transmitters and optoelectronic-detectors may be reduced, which in turn may increase battery life and/or allow use of physically smaller batteries for a more compact design. In some examples, narrow-beam optoelectronic-transmitters may be used to transmit optical signals with a narrow spectral range as described with reference to FIG. 5.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
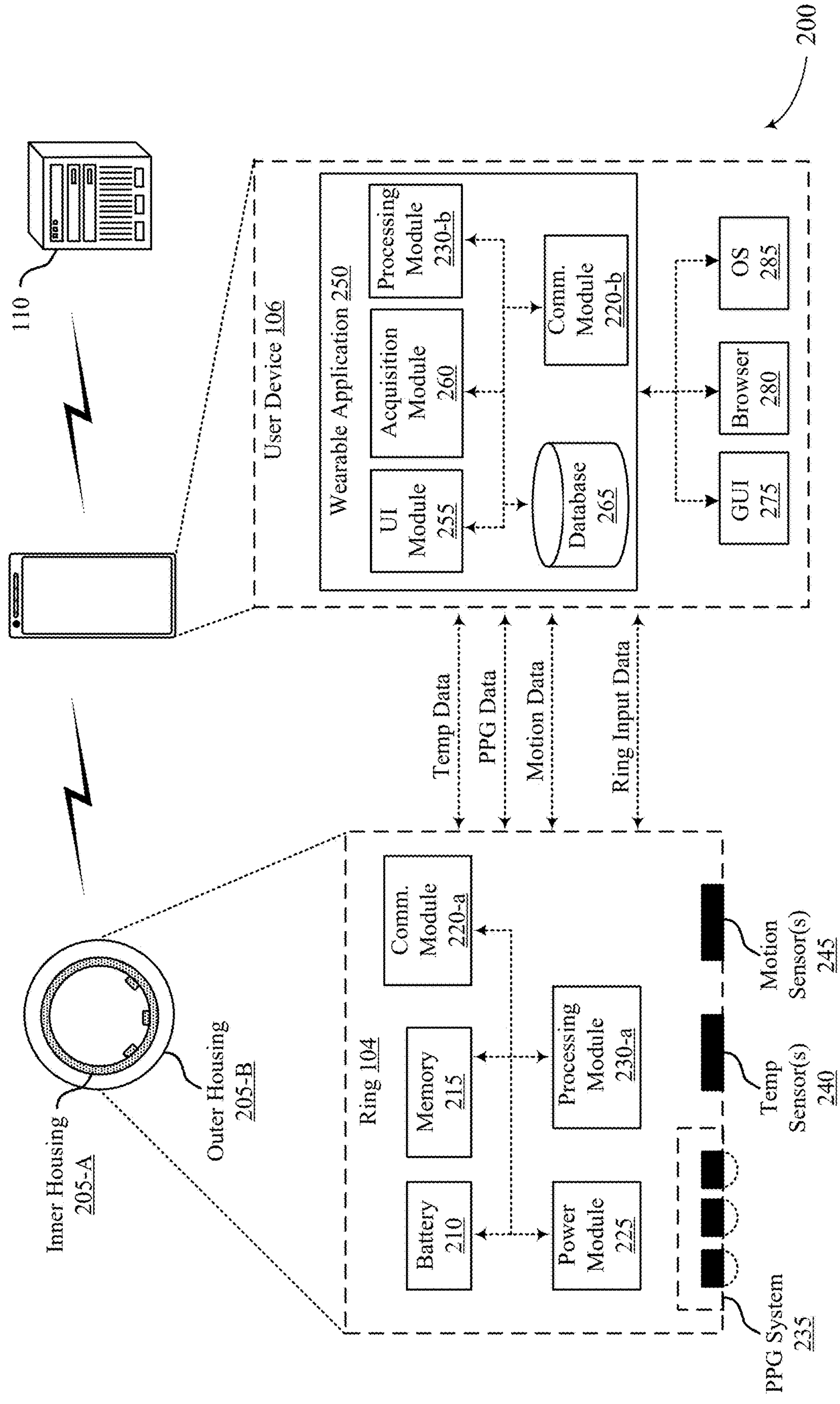
FIG. 2 illustrates an example of a system that supports optical sensing in a wearable device in accordance with aspects of the present disclosure.

FIG. 2 illustrates an example of a system 200 that supports optical sensing in a wearable device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing

205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers (also referred to as optoelectronic-detectors) that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as “derived values.” The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user’s finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user’s physiological parameters may be measured by sensors included on a ring 104, other devices may measure a user’s physiological parameters. For example, although a user’s temperature may be measured by a temperature sensor 240 included in a ring 104, other devices may measure a user’s temperature. In some examples, other wearable devices (e.g., wrist devices) may include sensors that measure user physiological parameters. Additionally, medical devices, such as external medical devices (e.g., wearable medical devices) and/or implantable medical devices, may measure a user’s physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., “app”) that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

In some cases, the wearable device 104 and the user device 106 may be included within (or make up) the same device. For example, in some cases, the wearable device 104 may be configured to execute the wearable application 250, and may be configured to display data via the GUI 275.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, data collected by the wearable device 104, and/or analyses performed by the wearable device 104, the user device 106, and/or the servers 110, may be used to adjust operational parameters of the wearable device 104. For example, based on a determined heart rate of the user and/or a determined activity state of the user, the wearable device 104 may adjust a sampling rate for measuring the user's heart rate, and/or may activate or deactivate certain sensors and/or physiological measurements (e.g., deactivate SpO2 measurements when the user is engaged in physical activity, or otherwise exhibits an activity/movement level above some threshold). By way of another example, the user device 106 and/or the servers 110 may calculate a Readiness Score for the user, and may deactivate or disable activity measurements performed by the wearable device 104 in cases where the Readiness Score is below some threshold (in order to reduce power consumption and conserve battery at the wearable device 104, and/or to disincentivize the user from performing rigorous activity when their Readiness Score is below the threshold value). In this regard, any measurements, calculations, and/or analyses performed by the various devices within the system 100 (e.g., wearable device 104, user device 106, servers 110) may be used by the system 100 to control and/or adjust the operational parameters of the wearable device 104.

Operational parameters that may be controlled/adjusted at the wearable device 104 based on collected data and/or analyses performed by the system 100 may include, but are not limited to, a periodicity/frequency that measurements are performed (e.g., sampling rate), a power level or intensity of LEDs, algorithms used to analyze data at the wearable device 104, what types of measurements are performed (e.g., enabling/disabling specific sensors or types of measurements), a periodicity or frequency that the wearable device 104 transmits data to the user device 106, or any combination thereof. Adjusting operational parameters of the wearable device 104 based on collected data and/or analyses performed by the system 100 may reduce power consumption and improve battery performance at the wearable device 104, and may lead to higher quality data collected by the wearable device 104, thereby enabling the system 100 to perform more accurate and reliable analyses/diagnoses of the user's physiological parameters, and leading to better guidance and insights that may enable the user to improve their overall health.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

According to the designs described herein, the light-emitting components included in the wearable device 104 may include narrow-beam optoelectronic-transmitters that output narrow-beam optical signals for biometric data collection. A narrow-beam optical signal may be an optical signal that has an angular spread (e.g., beam width) comprising a full-width half-measure angular range of less than twenty degrees in polar coordinates. In other examples, a narrow-beam optical signal may be an optical signal that has an angular spread (e.g., beam width) comprising a full-width half-measure angular range of less than forty degrees in polar coordinates. As illustrated with respect to FIG. 4, with reference to a beam-width distribution curve, the term full-width half-measure (also referred to as full-width half-maximum) may represent the width of the curve measured between the two points where the curve's value is half its maximum. Among other advantages, use of narrow-beam optoelectronic-transmitters instead of wide-beam optoelectronic transmitters may improve the quality of biometric data collection, reduce power consumption, reduce the sizes of various components (e.g., apertures, material protrusions), and reduce the distances between various components (e.g., between optoelectronic-transmitters and optoelectronic-detectors).

Figure 3:
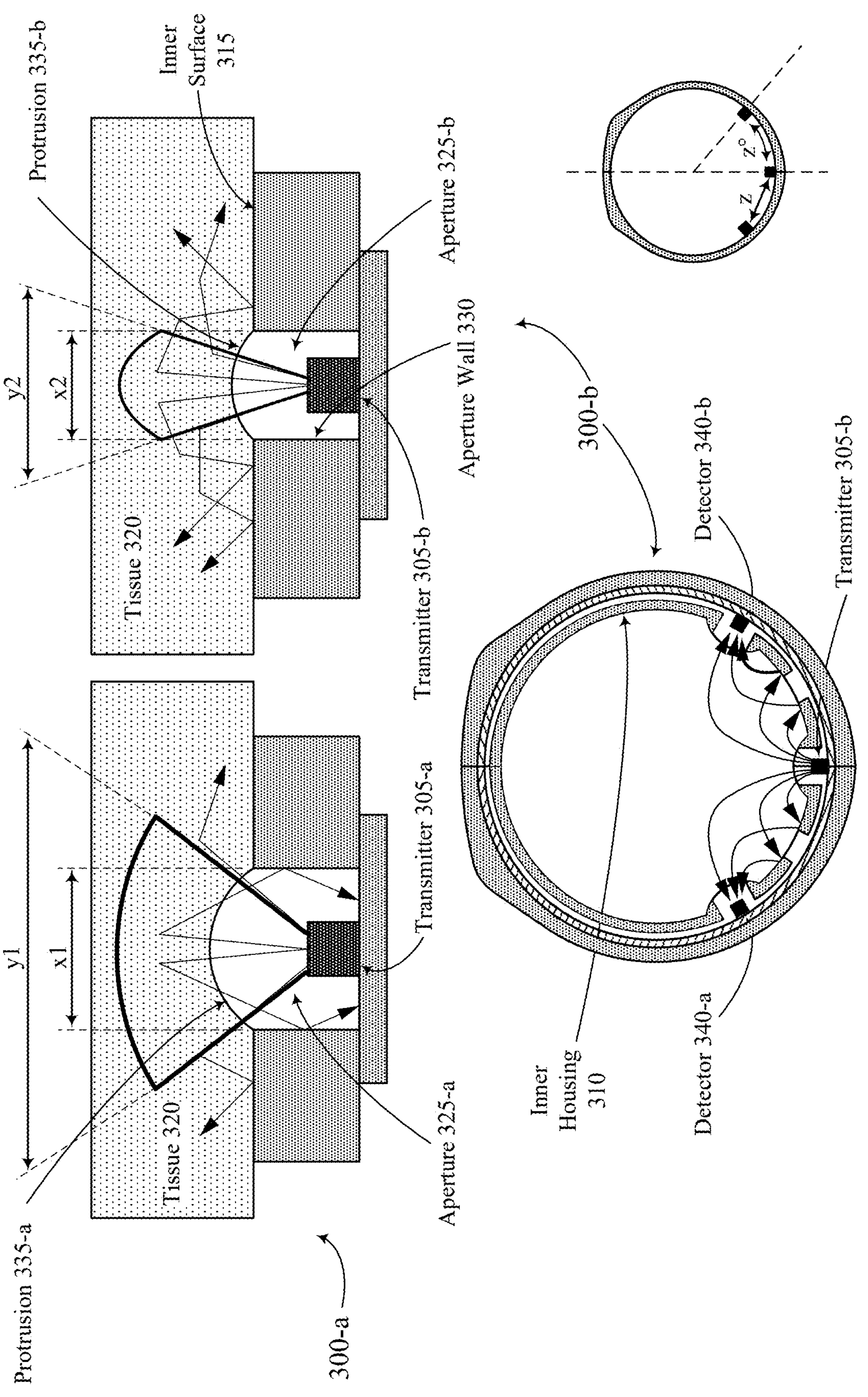
FIG. 3 shows an example of wearable devices that support optical sensing in a wearable device in accordance with aspects of the present disclosure.

FIG. 3 shows an example of wearable devices 300. The wearable devices 300 may include a wearable device 300-*a* that includes a wide-beam optoelectronic-transmitter 305-*a* and a wearable device 300-*b* that includes a narrow-beam optoelectronic-transmitter 305-*b*. The wearable device 300-*b* may include an inner housing 310 with an inner surface 315 that is configured to interface with the tissue 320 (e.g., skin) of a user. In some examples, the inner surface 315 may be made of or coated with a reflective material such as a metallic material, a ceramic material (e.g., with a metallic or white finish), a plastic material (e.g., with a metallic or white finish), or any combination thereof. Compared to a non-reflective material, use of a reflective material may increase the amount of light (e.g., optical signals) reflected into the tissue 320 and the optoelectronic-detectors (e.g., the optical signals may bounce between the tissue 320 and the reflective inner surface until they reach the optoelectronic-detectors 340).

As shown in FIG. 3, the various light sources (e.g., transmitters 305) and light detectors (e.g., detectors 340) may be positioned at different radial positions on/within the inner curved surface of the wearable device 300-*b* (where the radial positions may be separated by some quantity of degrees in polar coordinates, such as Z° illustrated in FIG. 3). Although shown with one optoelectronic-transmitter and two optoelectronic-detectors, other quantities and ratios of optoelectronic-transmitters and optoelectronic-detectors are contemplated and within the scope of the present disclosure.

The wide-beam optoelectronic-transmitter 305-*a* may output optical signals with an angular spread that has a full-width half-measure angular range of greater than eighty degrees (80°) in polar coordinates. The narrow-beam optoelectronic-transmitter 305-*b* may output optical signals with an angular spread that has a full-width half-measure angular range of less than twenty (20°) degrees in polar coordinates or less than forty (40°) degrees in polar coordinates. So, the beam-width y2 of the optical signals transmitted by the optoelectronic-transmitter 305-*b* may be smaller than the beam-width y1 of the optical signals transmitted by the optoelectronic-transmitter 305-*a*. Accordingly, the penetration depth (e.g., how far the optical signals penetrate into the tissue 320 of the user) of the optical signals transmitted by the optoelectronic-transmitter 305-*b* may be greater than the penetration depth of the optical signals transmitted by the optoelectronic-transmitter 305-*a*, which in turn may improve the quality of biometric data collected by the wearable device 300-*b* (e.g., without increasing power consumption). For example, compared to the optical signals output by the optoelectronic-transmitter 305-*a*, a greater proportion of the optical signals output by the optoelectronic-transmitter 305-*b* may reach the venous pulsating layers of the tissue 320.

The deeper penetration depths that may be achieved by the optoelectronic-transmitter 305-*a* may be particularly relevant in the context of finger-worn devices. Both finger-worn wearable ring devices and other types of wearable devices, such as wrist-worn wearable devices, may perform PPG measurements based on blood flow within "superficial" arteries that lie just below the surface of the tissue. However, as compared to other types of wearable devices such as wrist-worn devices, wearable ring devices worn on the finger may be more susceptible to rotation and other movement relative to the finger. That is, it may be easier (and more likely) that a wearable ring device becomes rotated on the user's finger as compared to a wrist-worn device being rotated on the user's wrist. As such, it is more common in the context of finger-worn devices that the sensors (e.g., transmitters 305, detectors 340) may be rotated further away from the arteries within the finger that are used for PPG measurements. In this regard, in cases where the wearable device 300-*b* becomes rotated on the user's finger, the deeper penetration depths that may be achieved by the optoelectronic-transmitter 305-*a* may still enable the wearable device 300-*b* to perform accurate and reliable physiological measurements despite the sensors of the ring being further from the arteries.

The wearable devices 300 may include one or more apertures 325 (e.g., cavities through the inner housing) within which optoelectronic-transmitters and optoelectronic-detectors are disposed. At least one dimension of the aperture 325-*b* may be based on (e.g., a function of, proportional to) the beam-width of the optical signals transmitted by the optoelectronic-transmitter 305-*b*.

For example, the size (e.g., height, width) of the aperture 325-*b* within which the optoelectronic-transmitter 305-*b* is disposed may be based on the beam-width of the optical signals transmitted by the optoelectronic-transmitter 305-*b* so that the aperture 325-*b* enables an entirety of the optical signal to propagate through the aperture 325-*b* across an entirety of the angular spread without clipping). So, the size of the aperture 325-*b* within which the optoelectronic-transmitter 305-*b* is disposed may be smaller than the size of the size of the aperture 325-*a* within which the optoelectronic-transmitter 305-*a* is disposed. For example, the width ×2 of the aperture 325-*b* may be smaller than the width ×1 of the aperture 325-*a*. Smaller-sized apertures may improve the quality of biometric signals collected by the wearable device 300-*b* by decreasing the amount of light reflected into the apertures, which in turn may decrease the amount of internal stray light measured by the optoelectronic-detectors, where internal stray light refers to optical signals that are reflected into an optoelectronic-detector through the body of the wearable device 300-*b*.

To reiterate, in some examples the size of an aperture 325-*b* may be such that aperture walls 330 do not block any portion (or block less than a threshold portion) of a narrow-beam optical signal transmitted by the optoelectronic-transmitter 305-*b*. Such a configuration may consume less power and reduce internal stray light relative to configurations that solely use clipping (e.g., physical blockage) of a wide-beam optical signal to create a narrow-beam optical signal. However, in some examples the use of aperture walls 330 to clip a narrow-beam optical signal may further improve biometric data collection. For instance, the aperture walls 330 may be highly reflective and angled (e.g., to act as conical reflectors) such that the light hitting them reflects to a narrower beam than that generated by the optoelectronic-transmitter 305-*b*.

In addition to improving functionality of the wearable device 300-*b*, use of narrow-beam optoelectronic-transmitters may allow for aesthetic improvements as well. For example, due to the greater received signal penetration depth (e.g., the penetration depth of the optical signals received by the optoelectronic-detectors 340) and decreased reflection through the apertures associated with narrow-beam optical signals, the wearable device 300-*b* may feature aperture walls 330 (e.g., the walls that define the apertures 325-*b*) that are a different color than the inner surface 315 (without significant loss in biometric data collection quality). Alternatively, the aperture walls 330 may be the same color as the inner surface 315 but surface area outlining or surrounding the apertures 325-*b* may be a different color than the rest of the inner surface 315. Alternatively, a first portion of an aperture wall 330 may be the same color as the inner surface 315 and a second portion of the aperture wall 330 may be a different color. Thus, in some examples, the aperture walls 330 may be made of or coated with a reflective material such as a metallic material, a ceramic material (e.g., with a metallic or white finish), a plastic material (e.g., with a metallic or white finish), or any combination thereof. Additionally, reducing the size of the apertures 325 may improve the appearance of the wearable device 300-*b*.

An optoelectronic-transmitter may be at least partially surrounded or covered by a material protrusion, e.g., in the form of a protrusion 335, that separates the optoelectronic-transmitter from the tissue 320 of the user. In some examples, the protrusion 335 may extend from the inner surface 315. At least one dimension of the protrusion 335 may be based on (e.g., a function of, proportional to) the beam-width of the optical signals transmitted by the optoelectronic-transmitter 305-*b*. For example, the size (e.g., height, width, radius, thickness) of the protrusion 335-*b* coupled with an optoelectronic-transmitter 305-*b* may be based on the beam-width of the optical signals transmitted by the optoelectronic-transmitter 305-*b*. So, the size of the protrusion 335-*b* coupled with the optoelectronic-transmitter 305-*b* may be smaller than the size of the protrusion 335-*a* coupled with the optoelectronic-transmitter 305-*a*. For example, the radius of the protrusion 335-*b* may be smaller than the radius of the protrusion 335-*a* which may improve comfort of the user wearing the wearable device 300-*b*.

The protrusion 335-*b* may improve contact with the tissue and protect the transmitter 305 against the environment. The protrusion 335-*b*, also referred to as a material protrusion, may be dome-shaped and may be an optically transparent material such as an epoxy material or a glass material. Relative to an epoxy material, use of a glass material may reduce light reflecting from an interface between the skin and the protrusion 335-*b*, which otherwise may result in a relatively lower quality of measurements. The glass may be formed into a dome shape and sealed to a housing of the wearable device to form a relatively more robust hollow dome-shaped protrusion that may result in relatively higher quality of measurements (e.g., as compared to some other optically transparent materials, such as epoxy). In some examples, the dome-shaped protrusions may be formed from a sheet of glass that is curved into a molded shape or from an unmolded glass pre-form that is pressed into the molded shape. In some examples, the glass may be bonded with the housing of the wearable device during the molding process (e.g., with the housing forming a portion of the mold for the dome-shaped protrusion) or following the molding process.

The use of glass for the apertures and/or protrusions 335 through which light is transmitted/received by the wearable device 300-*b* may offer other advantages. For example, epoxy and other polymers include light absorption peaks within the short wavelength infrared (SWIR) range of the light-sources used by the wearable device 300-*b*, which may partially block the measurement signal of light within the SWIR range. However, glass may not have such absorption peaks, and may therefore lead to higher signal quality as compared to other materials.

In some examples (e.g., in examples in which the protrusion 335-*b* is formed of a glass material), the protrusion 335-*b* may include one or more optical coatings or reflective surfaces to improve optical measurements. For example, the one or more reflective surfaces may be positioned to reflect at least a portion of the light emitted from the transmitter 305-*b*. The one or more reflective surfaces are configured to modify a set of characteristics of a light emission pattern of the light sources towards the detectors 340. In such cases, the one or more reflective surfaces may help direct or focus the light emission pattern of the one or more light sources to be directionally towards the field of view of the detectors, thereby decreasing an amount of noise in the signal and increasing the efficiency and accuracy of the signal. Thus, use of one or more reflective surfaces on a surface of the protrusion 335-*b* may lead to more accurate physiological data measurements.

The optical functioning of the transmitter 305-*b* may be enhanced with the different kinds of coatings without a large increase in sensor structure thickness (e.g., overall thickness of the transmitter 305-*b* and thereby the thickness of the wearable device 300). For example, changing the coating of the protrusion 335-*b* may be used for changing an emission pattern of the transmitter 305-*b* and/or a field of view of the detectors 340.

The protrusion 335-*b* may include one or more reflective surfaces. The reflective surfaces may be formed from one or more coatings applied to the protrusion 335-*b*. Additionally, or alternatively, the reflective surfaces may be formed from one or more reflective components that are adhered to or embedded within the protrusion 335. By using different kinds of reflective surfaces on top of or embedded within the protrusion 335-*b*, and by positioning them with respect to the transmitter 305-*b*, a light emission pattern of the transmitter 305-*b* may be modified. The reflective surfaces may be configured to alter the light pattern of the light emitted from the transmitter 305-*b* by reflecting light, focusing light, redirecting light, or any combination thereof. For example, the protrusion 335-*b* may include a single reflective surface positioned on the outer surface of the protrusion 335-*b* (e.g., the reflective surface may be adhered to the top of the dome-shaped protrusion 335-*b*). In some cases, the reflective surface may be positioned on the inner surface of the protrusion 335-*b*.

The optical signals transmitted by the optoelectronic-transmitter 305-*b* may be detected and measured by the optoelectronic-detectors 340 so that biometric data can be derived from various characteristics of the optical signals. The distance between the optoelectronic-transmitter 305-*b* and an optoelectronic-detector may be based on (e.g., a function of, proportional to) the penetration depth of the optical signals transmitted by the optoelectronic-transmitter 305-*b* (e.g., because a greater concentration of the optical signals is reflected closer to the optoelectronic-transmitter 305-*b*). So, the distance between the optoelectronic-transmitter 305-*b* and an optoelectronic-detector may be based on (e.g., a function of, proportional to) the beam-width of the optical signals transmitted by the optoelectronic-transmitter 305-*b*. Thus, the distances between the optoelectronic-transmitter 305-*b* and the optoelectronic-detectors 340 may be less than the distances between the optoelectronic-transmitter 305-*a* and corresponding optoelectronic-detectors (not shown) of wearable device 300-*a*. The distance z between the optoelectronic-transmitter 305-*b* and an optoelectronic-detector 340 may be the radial distance (e.g., z degrees in polar coordinates) or the point-to-point distance (e.g., z mm).

Thus, the wearable device 300-*b* may include one or more narrow-beam optoelectronic transmitters, which in turn may improve the quality of biometric data collection, reduce the sizes of various components (e.g., apertures, epoxy bumps), and reduce the distances between various components (e.g., between optoelectronic-transmitters and optoelectronic-detectors).

In some examples, the wearable device 300-*b* may measure the signal absorption of emitted light at different wavelengths using one or more sensor arrangements. In the illustrated example, the wearable device 300-*b* includes a single transmitter 305-*b* that covers a wide range of wavelengths (e.g., around 1100 nm) and two detectors 340. The detectors 340-*a* may be coated to filter out wavelengths below a threshold wavelength (e.g., 1180 nm), and the detector 340-*b* may be coated to filter out wavelengths above the threshold wavelength in order to determine the signal absorption points and estimate the change in the temperature of the blood. That is, the wearable device 300-*b* of the present disclosure may be configured to use SWIR wavelength ranges to enable various measurements and use cases, including measurement of blood temperature, determining a presence or concentration of various materials (e.g., lipids, metabolites, water), determining or estimating a level of hydration, and the like. In particular, the wearable device 300-*b* may be configured to measure absorption of various spectral ranges, where the varying levels of absorption may be used to identify or otherwise measure a presence, quantity, or concentration of various materials/components that absorb light in the respective spectral ranges.

In another example, the wearable device 300-*b* may include a single transmitter 305-*b* that covers a wide range of wavelengths and a single detector 340. The spectrometer may split the specific wavelengths spatially to generate signal absorption points, which can be used to estimate the change in temperature of the blood. That is, the wearable device 300-*b* may be configured to analyze absorptions across different spectral ranges of light, where the different absorptions may be used to determine/estimate changes in temperature of the user's blood (and therefore estimate skin and/or body temperature). In another example, the wearable device 300-*b* may include two transmitters 305-*b* and one detector 340. The first transmitter may emit light at a wavelength above a first threshold wavelength (e.g., 1160 nm), and the second transmitter may emit light at a wavelength above a second threshold wavelength (e.g., 1190 nm). In such an example, the single detector measures the respective light signals and compares the two signal absorption peaks values (e.g., spectral points) to determine a change in a physiological characteristic (e.g., blood temperature).

In some implementations, wearable device 300-*b* (e.g., wearable ring device) may include both narrow-beam light source(s) (e.g., optoelectronic-transmitter 305-*b*) and wide-beam light source(s) (e.g., optoelectronic-transmitter 305-*a*). The narrow-beam and wide-beam light sources may be positioned at different radial positions along the inner curved surface of the wearable device 300-*b*, as described herein. In such cases, the wearable device 300-*b* may be able to monitor the relative quality of physiological data measured from the user using the narrow-beam and wide-beam light sources, and may selectively activate or deactivate the narrow-beam and wide-beam light sources based on the relative quality of data. That is, the wearable device may be able to switch between narrow-beam and wide-beam light sources for collecting physiological data, which may result in more accurate and reliable physiological data. The wearable device 300-*b* may switch between different types of light sources (e.g., between narrow-beam and wide-beam light sources) based on the relative quality of data collected via the respective types of light sources, based on the power consumption of the respective types of light sources, based on the types of measurements to be performed, based on the battery level of the wearable device 300-*b*, or any combination thereof.

For example, as described herein, in cases where the wearable device 300-*b* becomes rotated on the user's finger (thereby moving the sensors further from the arteries within the finger), the relatively shallower penetration depths achieved using wide-beam light sources may not be sufficient to capture high quality PPG data. As such, in this example, the wearable device 300-*b* may be configured to identify the decrease in signal quality using the wide-beam light sources, and may be configured to switch to the narrow-beam light sources in order to achieve deeper light penetration depths, which may result in higher signal/PPG data quality.

Figure 4:
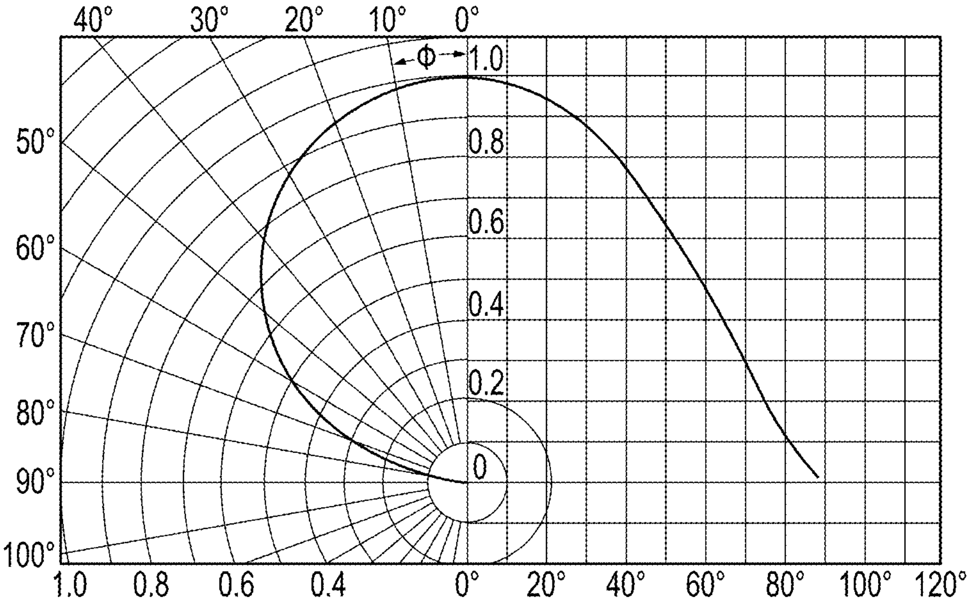
FIG. 4 shows an example of a radiation plot that supports optical sensing in a wearable device in accordance with aspects of the present disclosure.
Figure 4:
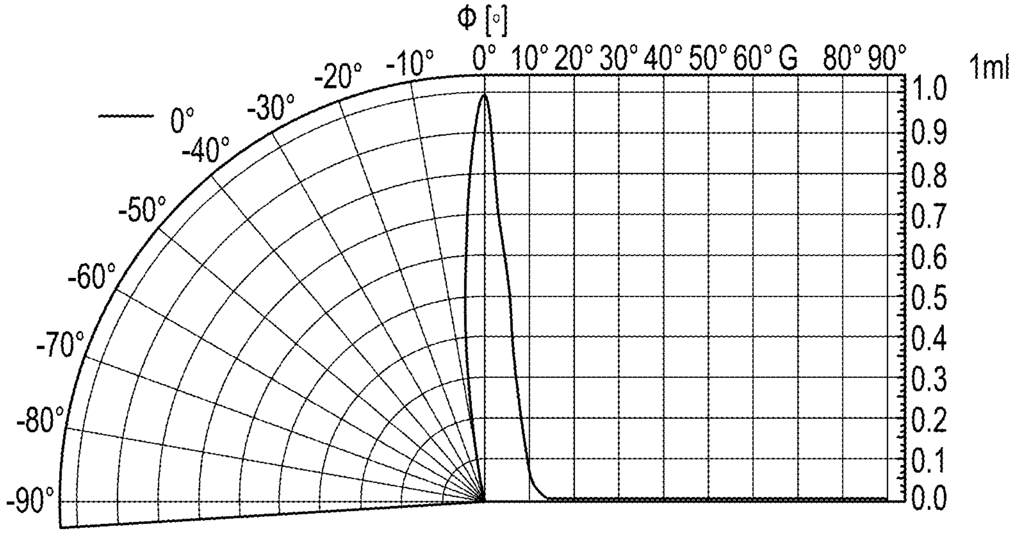

FIG. 4 shows an example of radiation plots 400. The radiation plots 400 include radiation plot 400-*a*, which may represent the radiation pattern of a wide-beam optoelectronic-transmitter, and radiation plot 400-*b*, which may represent the radiation pattern of a narrow-beam optoelectronic-transmitter. As illustrated, an optical signal transmitted by the wide-beam optoelectronic-transmitter may have an angular spread (e.g., beam width) with a full-width half-measure angle of greater than 80° in polar coordinates. In contrast, an optical signal transmitted by the narrow-beam optoelectronic-transmitter may have an angular spread (e.g., beam width) with a full-width half-measure angle of less than 20° in polar coordinates or less than 40° in polar coordinates. The full-width half-measure of an optical signal's angular spread may be the distance, in degrees, between the two points at which the optical signal's magnitude is at half-strength.

Figure 5:
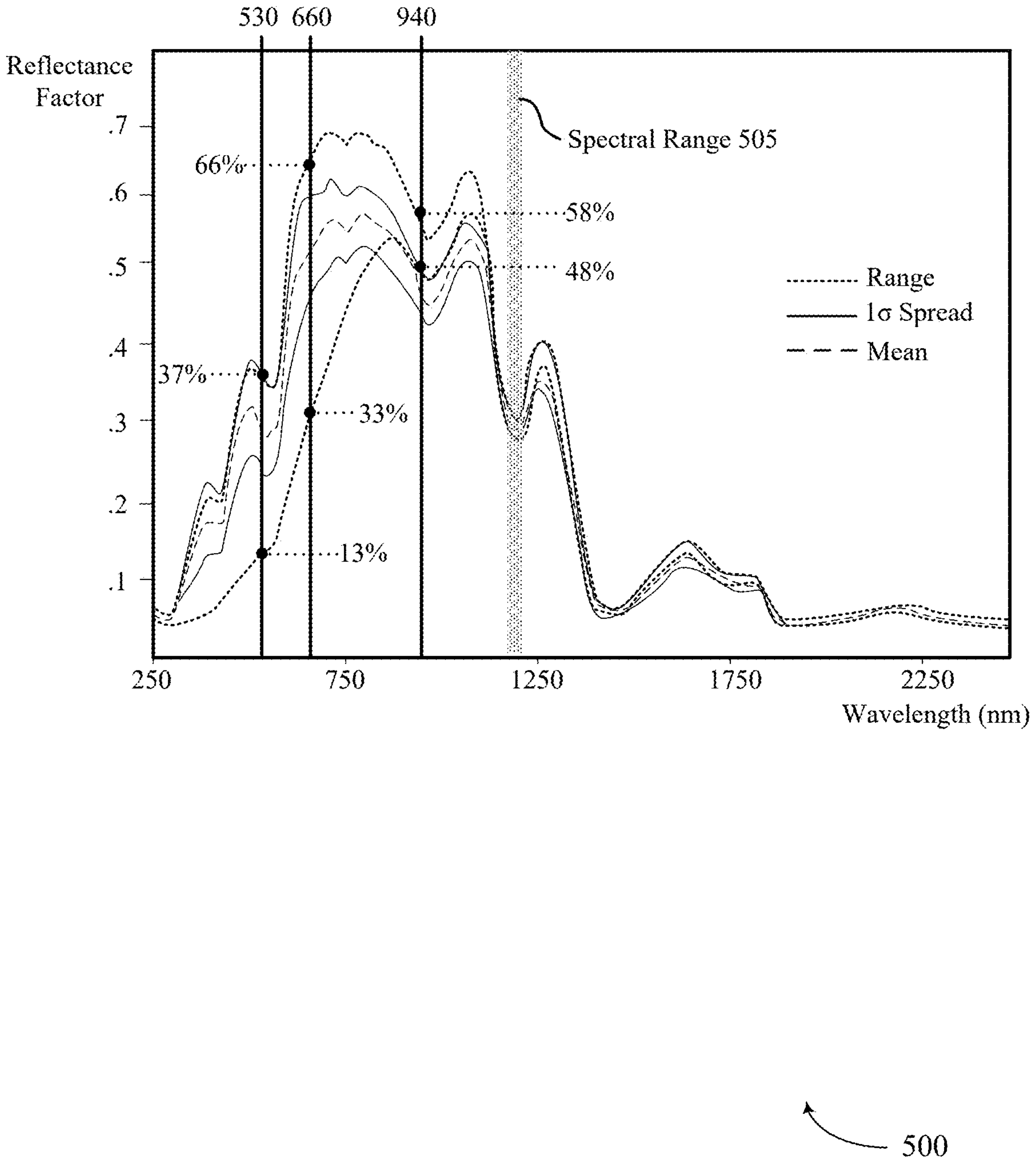
FIG. 5 shows an example of a plot that supports optical sensing in a wearable device in accordance with aspects of the present disclosure.

FIG. 5 shows an example of a plot 500 that supports optical sensing in a wearable device in accordance with aspects of the present disclosure. The plot 500 shows the reflectance factor of human skin (from a diverse population of skin tones) as a function of wavelength. The dotted lines represent the upper and lower boundaries of the range of the reflectance factor, the solid lines represent the 1σ deviation of the reflectance factor, and the dashed line represents the mean of the reflectance factor. As can be seen from plot 500, the reflectance factor varies widely at some wavelengths (e.g., ~700 nm) and varies less widely at other wavelengths (e.g., –1100 nm). For example, the skin reflectance factor may range between 13% and 37% at green wavelengths (e.g., –530 nm), and may range between 33% and 66% at red wavelengths (e.g., –660 nm), and may range between 48% and 58% at infrared wavelengths (e.g., –940 nm).

In general, the reflectance factor may vary less at higher wavelengths (e.g., wavelengths>1000 nm). In some examples, optoelectronic-transmitters may be used to transmit optical signals with higher wavelengths (e.g., wavelengths>1000 nm) and narrow spectral ranges (e.g., wavelength ranges~200 nm), which may improve the quality of biometric data collection (e.g., due to lower skin reflectance variation at those wavelengths/ranges). Although higher wavelength, narrow spectral range optical signals may be transmitted by either wide-beam optoelectronic-transmitters or narrow-beam optoelectronic transmitters, use of narrow-beam optoelectronic transmitters may provide additional benefits as described herein. In some examples, the optoelectronic-transmitters may be configured to transmit optical signals with spectral range 505 (e.g., 1000-1500 nm), which may be a range at which the absorption coefficient of water is below a threshold. Moreover, it has been found that there are light-absorbing tissue compounds within this wavelength range that are related to body metabolites. As such, optoelectronic-transmitters that emit light within this wavelength range may be used to identify and/or measure such tissue compounds and body metabolites, such as lipid (fat) measurements. In some examples, the optoelectronic-transmitters may be configured to transmit optical signals with a wavelength that is approximately 1100 nm. Other spectral ranges with lower boundaries that are greater than 1000 nm are contemplated and within the scope of the present disclosure.

Thus, in some examples, optoelectronic-transmitters such as narrow-beam optoelectronic transmitters may be used to transmit optical signals with relatively high and narrow spectral ranges, which may further improve the quality of biometric data collection.

It should be noted that the methods described above describe possible implementations, and that the operations and the steps may be rearranged or otherwise modified and that other implementations are possible. Furthermore, aspects from two or more of the methods may be combined.

An apparatus is described. The apparatus may include a housing comprising a reflective inner surface configured to at least partially contact a tissue of a user when the wearable device is worn by the user, an optoelectronic-transmitter configured to output an optical signal with an angular spread comprising a full-width half-measure angular range of less than twenty degrees in polar coordinates, the optoelectronic-transmitter at least partially covered with an epoxy protrusion extending from the reflective inner surface, wherein a radius, a height, or both, of the epoxy protrusion is based at least in part on the angular spread, an aperture disposed within the reflective inner surface of the housing and configured to enable propagation of the optical signal through the housing, wherein a width of the aperture is based at least in part on the angular spread and permits propagation of the optical signal within the angular spread, and an optoelectronic-detector configured to receive the optical signal, wherein a distance between the optoelectronic-transmitter and the optoelectronic-detector is based at least in part on the angular spread.

In some examples of the apparatus, the optoelectronic-transmitter comprises a VCSEL, a laser diode, a narrow-beam LED, a RCLED, or any combination thereof.

In some examples of the apparatus, the optical signal may be associated with a wavelength greater than 1000 nanometers and the wearable device may be configured to collect biometric data for a user based at least in part on the optical signal.

In some examples of the apparatus, the optical signal may be associated with a wavelength between 1000 nanometers and 1500 nanometers and the wearable device may be configured to collect biometric data for a user based at least in part on the optical signal.

Some examples of the apparatus may further include a second optoelectronic-detector configured to receive the optical signal, wherein a second distance between the optoelectronic-transmitter and the second optoelectronic-detector may be based at least in part on the angular spread.

In some examples of the apparatus, at least one wall of the aperture comprises a different color relative to the reflective inner surface.

In some examples of the apparatus, the reflective inner surface may be configured to reflect portions of the optical signal that exit the tissue of the user back into the tissue of the user for detection by the optoelectronic-detector.

In some examples of the apparatus, the height of the epoxy protrusion may be based at least in part on the width of the aperture and the angular spread.

In some examples of the apparatus, the width of the aperture may be sized to enable an entirety of the optical signal to propagate through the aperture across an entirety of the angular spread without clipping.

In some examples of the apparatus, the optical signal emitted by the optoelectronic-transmitter may be associated with a wavelength, the wavelength may be associated with a range of skin reflectance values that indicate a relative level of absorption or reflection of the wavelength by the tissue of the user, and the range of skin reflectance values may be less than a threshold range.

In some examples of the apparatus, the wavelength comprises approximately 1100 nanometers.

In some examples of the apparatus, the wearable device comprises a wearable ring device.

In some examples of the apparatus, the reflective inner surface comprises a metallic material, a ceramic material, a plastic material, or any combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device configured to be worn on a finger of a user, the wearable ring device comprising:

a housing comprising a reflective inner surface configured to at least partially contact a tissue of the user when the wearable ring device is worn by the user;

an optoelectronic-transmitter configured to output, through the reflective inner surface, an optical signal with an angular spread comprising a full-width half-measure angular range of less than twenty degrees in polar coordinates, the optoelectronic-transmitter at least partially covered with a material protrusion extending from the reflective inner surface, wherein a radius, a height, or both, of the material protrusion is based at least in part on the angular spread;

an aperture disposed within the reflective inner surface of the housing and configured to enable propagation of the optical signal through the housing, wherein a width of the aperture is based at least in part on the angular spread and permits propagation of the optical signal within the angular spread; and an optoelectronic-detector configured to receive the optical signal, wherein a distance between the optoelectronic-transmitter and the optoelectronic-detector is based at least in part on the angular spread.

2. The wearable ring device of claim 1, wherein the optoelectronic-transmitter comprises a vertical-cavity surface-emitting laser (VCSEL), a laser diode, a narrow-beam light-emitting diode (LED), a resonant cavity light emitting diode (RCLED), or any combination thereof.

3. The wearable ring device of claim 1, wherein the optical signal is associated with a wavelength greater than 1000 nanometers, and wherein the wearable ring device is configured to collect biometric data for the user based at least in part on the optical signal.

4. The wearable ring device of claim 1, wherein the optical signal is associated with a wavelength between 1000 nanometers and 1500 nanometers, and wherein the wearable ring device is configured to collect biometric data for the user based at least in part on the optical signal.

5. The wearable ring device of claim 1, further comprising:

a second optoelectronic-detector configured to receive the optical signal, wherein a second distance between the optoelectronic-transmitter and the second optoelectronic-detector is based at least in part on the angular spread.

6. The wearable ring device of claim 1, wherein at least one wall of the aperture comprises a different color relative to the reflective inner surface.

7. The wearable ring device of claim 1, wherein the reflective inner surface is configured to reflect portions of the optical signal that exit the tissue of the user back into the tissue of the user for detection by the optoelectronic-detector.

8. The wearable ring device of claim 1, wherein the height of the material protrusion is based at least in part on the width of the aperture and the angular spread.

9. The wearable ring device of claim 1, wherein the width of the aperture is sized to enable an entirety of the optical signal to propagate through the aperture across an entirety of the angular spread without clipping.

10. The wearable ring device of claim 1, wherein the optical signal emitted by the optoelectronic-transmitter is associated with a wavelength, the wavelength is associated with a range of skin reflectance values that indicate a relative level of absorption or reflection of the wavelength by the tissue of the user, and the range of skin reflectance values is less than a threshold range.

11. The wearable ring device of claim 10, wherein the wavelength comprises approximately 1100 nanometers.

12. The wearable ring device of claim 1, wherein the optoelectronic-transmitter is positioned within or beneath the reflective inner surface at a first radial position, the wearable ring device further comprising:

at least one light-emitting diode (LED) positioned within or beneath the reflective inner surface at a second radial position that is different from the first radial position, the at least one LED configured to output a second optical signal with an angular spread comprising a full-width half-measure angular range that is greater than eighty degrees in polar coordinates.

13. The wearable ring device of claim 12, further comprising one or more processors communicatively coupled with the optoelectronic-transmitter, the optoelectronic-detector, and the at least one LED, wherein the one or more processors are configured to cause the wearable ring device to:

measure first physiological data associated with the user using the at least one LED;

determining a signal quality metric associated with the first physiological data collected via the at least one LED;

selectively activate the optoelectronic-transmitter and deactivate the at least one LED based at least in part on the signal quality metric; and measure second physiological data associated with the user using the optoelectronic-transmitter.

14. The wearable ring device of claim 1, wherein the reflective inner surface comprises a metallic material, a ceramic material, a plastic material, or any combination thereof.

15. The wearable ring device of claim 1, wherein one or more walls of the aperture comprises a metallic material, a ceramic material, a plastic material, or any combination thereof.

16. A wearable device, comprising:

a housing comprising a reflective inner surface configured to at least partially contact a tissue of a user when the wearable device is worn by the user;

an optoelectronic-transmitter configured to output, through the reflective inner surface, an optical signal with an angular spread comprising a full-width half-measure angular range of less than twenty degrees in polar coordinates, the optoelectronic-transmitter at least partially covered with a material protrusion extending from the reflective inner surface, wherein a radius, a height, or both, of the material protrusion is based at least in part on the angular spread;

an aperture disposed within the reflective inner surface of the housing and configured to enable propagation of the optical signal through the housing, wherein a width of the aperture is based at least in part on the angular spread and permits propagation of the optical signal within the angular spread; and an optoelectronic-detector configured to receive the optical signal, wherein a distance between the optoelectronic-transmitter and the optoelectronic-detector is based at least in part on the angular spread.

17. The wearable device of claim 16, wherein the optoelectronic-transmitter comprises a vertical-cavity surface-emitting laser (VCSEL), a laser diode, a narrow-beam light-emitting diode (LED), a resonant cavity light emitting diode (RCLED), or any combination thereof.

18. The wearable device of claim 16, wherein the optical signal is associated with a wavelength greater than 1000 nanometers, and wherein the wearable device is configured to collect biometric data for the user based at least in part on the optical signal.

19. The wearable device of claim 16, wherein the optical signal is associated with a wavelength between 1000 nanometers and 1500 nanometers, and wherein the wearable device is configured to collect biometric data for the user based at least in part on the optical signal.

20. The wearable device of claim 16, further comprising:

a second optoelectronic-detector configured to receive the optical signal, wherein a second distance between the optoelectronic-transmitter and the second optoelectronic-detector is based at least in part on the angular spread.

* * * * *